United States Patent
Makino et al.

(10) Patent No.: US 9,326,680 B2
(45) Date of Patent: May 3, 2016

(54) OPHTHALMIC APPARATUS

(71) Applicant: NIDEK CO., LTD., Gamagori-shi, Aichi (JP)

(72) Inventors: Kenichiro Makino, Gamagori (JP); Hirokazu Nakamura, Nishio (JP); Daisuke Baba, Okazaki (JP); Toshiya Kobayashi, Kariya (JP)

(73) Assignee: NIDEK CO., LTD., Gamagori-shi (JP)

( * ) Notice: Subject to any disclaimer, the term of this patent is extended or adjusted under 35 U.S.C. 154(b) by 145 days.

(21) Appl. No.: 13/921,589

(22) Filed: Jun. 19, 2013

(65) Prior Publication Data

US 2014/0009740 A1  Jan. 9, 2014

(30) Foreign Application Priority Data

Jul. 3, 2012 (JP) .................................. 2012-149695
Jul. 3, 2012 (JP) .................................. 2012-149696

(51) Int. Cl.
*A61B 3/10* (2006.01)
*A61B 3/13* (2006.01)
(Continued)

(52) U.S. Cl.
CPC . *A61B 3/14* (2013.01); *A61B 3/132* (2013.01); *A61B 3/152* (2013.01); *G02B 21/248* (2013.01); *G02B 21/26* (2013.01)

(58) Field of Classification Search
CPC .. A61B 3/0016; A61B 3/0075; A61B 3/0083; A61B 3/132; A61B 3/14; A61B 3/152; A61B 3/154
USPC .................. 351/205, 206, 245, 246
See application file for complete search history.

(56) References Cited

U.S. PATENT DOCUMENTS 3,402,308 A * 9/1968 Henschke ................ H02K 7/06
                                                                     310/66
5,406,076 A * 4/1995 Mimura ................... G01D 5/36
                                                                     250/229

(Continued)

FOREIGN PATENT DOCUMENTS

GB  2 126 745 A  3/1984
JP  S62-130187 A  6/1987

(Continued)

OTHER PUBLICATIONS

Haydon Kerk, Liner Motion Catalog and Design Guide, "Stepper Motor Technical Overview: Tutorial," Jan. 2013.*

(Continued)

*Primary Examiner* — Thomas K Pham
*Assistant Examiner* — Nicholas R Pasko
(74) *Attorney, Agent, or Firm* — Oliff PLC

(57) ABSTRACT

An ophthalmic apparatus includes: a main unit including a unit for observing or photographing an examinee's eye; a movable part in which the main unit is mounted; a vertical movement mechanism provided with a drive part to move the movable part up and down; an operating member to be operated by an examiner to move the movable part up and down; a sensing part to detect an operation signal of the operating member; and a driving control part to convert the operation signal detected by the sensing part to a drive signal to move the movable part up and down, and drive the drive part based on the drive signal, wherein the drive part includes a motor having a hollow portion about a rotation axis thereof, the motor being controlled by the driving control part to rotate.

7 Claims, 7 Drawing Sheets

(51) Int. Cl.
*A61B 3/14* (2006.01)
*A61B 3/15* (2006.01)
*G02B 21/24* (2006.01)
*G02B 21/26* (2006.01)

(56) References Cited

U.S. PATENT DOCUMENTS

| | | | | |
|---|---|---|---|---|
| 5,471,260 A | | 11/1995 | Luce et al. | |
| 5,500,696 A | * | 3/1996 | Masuda | A61B 3/107 351/205 |
| 5,532,769 A | * | 7/1996 | Miwa | A61B 3/145 351/205 |
| 5,587,748 A | * | 12/1996 | Luce | A61B 3/0075 351/205 |
| 5,696,573 A | * | 12/1997 | Miwa | A61B 3/152 351/205 |
| 5,841,502 A | * | 11/1998 | Miwa | A61B 3/152 351/209 |
| 6,439,719 B2 | * | 8/2002 | Hayashi | A61B 3/152 351/208 |
| 2012/0050670 A1 | * | 3/2012 | Nakahara | A61B 3/152 351/206 |

FOREIGN PATENT DOCUMENTS

| | | | |
|---|---|---|---|
| JP | A-6-7292 | | 1/1994 |
| JP | H06-35529 A | | 2/1994 |
| JP | H10-507391 A | | 7/1998 |
| JP | H11-151631 A | | 6/1999 |
| JP | A-2001-83429 | | 3/2001 |
| JP | 2012045236 A | * | 3/2012 |
| JP | A-2012-45236 | | 3/2012 |
| WO | WO 96/13200 A1 | | 5/1996 |

OTHER PUBLICATIONS

English machine translation of Makino et al.*
Haydon Kerk, Linear Motion Catalog and Design Guide, "Stepper Motor Technical Overview: Tutorial," Jan. 2013.*
Nov. 4, 2013 Extended Search Report issued in European Patent Application No. 13173867.6.

* cited by examiner

OPHTHALMIC APPARATUS

CROSS-REFERENCE TO RELATED APPLICATIONS

This application is based upon and claims the benefit of priority from each of the prior Japanese Patent Applications Nos. 2012-149695 and 2012-149696 both filed on Jul. 3, 2012, the entire contents of which are incorporated herein by reference.

BACKGROUND OF THE INVENTION

1. Field of the Invention

The present invention relates to an ophthalmic apparatus for observing or photographing an examinee's eye.

2. Related Art

In an ophthalmic apparatus, a main unit containing an illumination system and an observation system is moved up and down to align the apparatus with an examinee's eye. For instance, in a slit-lamp microscope called a slit lamp, a mechanical up-and-down (vertical) movement mechanism is generally used. This mechanically transmits rotation of a joystick which is an operating member to a feed screw via gears and others. The main unit (the illumination system and the observation system) is thus synchronously moved up and down with respect to the eye (e.g., see Patent Document 1).

On the other hand, in an ophthalmic apparatus such as an automatic refractometer, an electrically-driven vertical movement mechanism is generally used. The rotation of a joystick is electrically detected and, based on a detection result thereof, the vertical movement mechanism is driven (e.g., see Patent Document 2). In the case of the conventional electrically-driven vertical movement mechanism, the rotation of a motor is transmitted to a feed screw and, in sync therewith, the main unit is moved with respect to an examinee's eye.

RELATED ART DOCUMENTS

Patent Documents

Patent Document 1: JP2001-83429A
Patent Document 2: JP06(1994)-7292A

SUMMARY OF INVENTION

Problems to be Solved by the Invention

In the case of the mechanical vertical movement mechanism, the movement of the main unit is performed in linear synchronization with operation by an examiner. This is effective in fine, or small, alignment. However, for a heavy main unit, a relatively large force is required to operate the joystick. This causes a delay in adjustment of the main unit to a desired position by the examiner, which may impede appropriate observation and photographing. On the other hand, the conventional electrically-driven vertical movement mechanism is configured to transmit the operation of the joystick to the main unit via a plurality of mechanical parts or components such as the gears and the screws. This causes a slow response speed of the vertical movement mechanism to the operation by the examiner and impedes smooth alignment adjustment.

Another problem is caused in a configuration that the main unit is electrically moved up and down in response to an input signal from the joystick. Specifically, in the case of coarse (rough) adjustment, the joystick is relatively fast rotated, so that signals are continuously inputted from the joystick to move the main unit up and down. Thus, the main unit is smoothly moved up and down. On the other hand, in the case of small (fine) adjustment, the joystick is relatively slowly rotated, signals are discretely inputted from the joystick, so that the main unit is moved up and down discretely (that is, time intervals are created between activation and non-activation), which may cause vibrations. The above situations lead to a problem that, during observation with high magnification power using a slit lamp or the like, an image is blurred and hard to observe.

The present invention has been made to solve the above problems in the conventional arts and has a purpose to provide an ophthalmic apparatus capable of appropriately moving up and down to perform observation and photographing.

Means of Solving the Problems

To achieve the above purpose, one aspect of the invention provides an ophthalmic apparatus including: a main unit including a unit for observing or photographing an examinee's eye; a movable part in which the main unit is mounted; a vertical movement mechanism provided with a drive part to move the movable part up and down; an operating member to be operated by an examiner to move the movable part up and down; a sensing part to detect an operation signal of the operating member; and a driving control part to convert the operation signal detected by the sensing part to a drive signal to move the movable part up and down, and drive the drive part based on the drive signal, wherein the drive part includes a motor having a hollow portion about a rotation axis thereof, the motor being controlled by the driving control part to rotate.

Effects of the Invention

According to the invention, an ophthalmic apparatus can be provided capable of appropriately moving up and down to perform observation and photographing.

DESCRIPTION OF EMBODIMENTS

Figure 1:
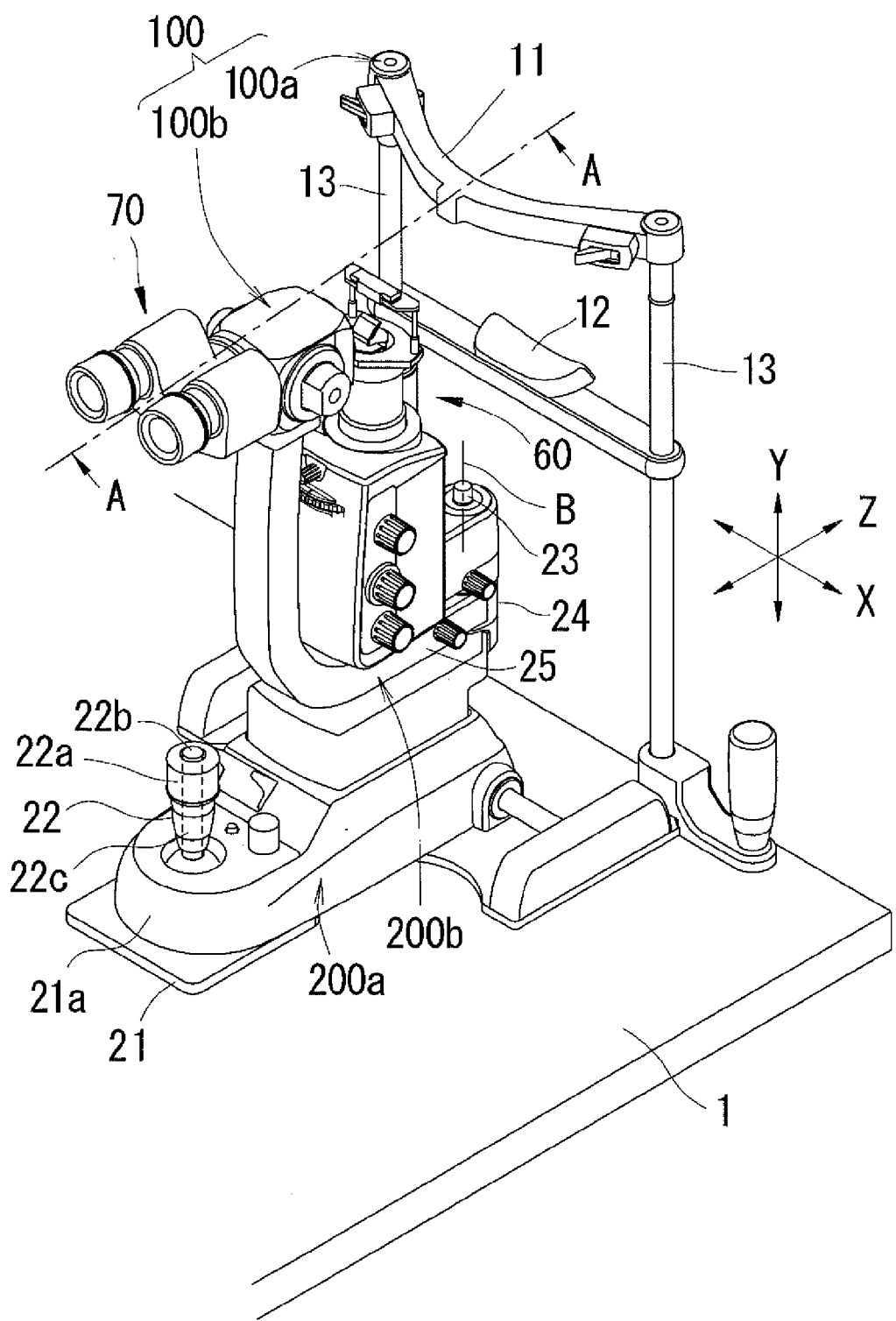
FIG. 1 is a perspective external view of a slit lamp of an embodiment.
Figure 2:
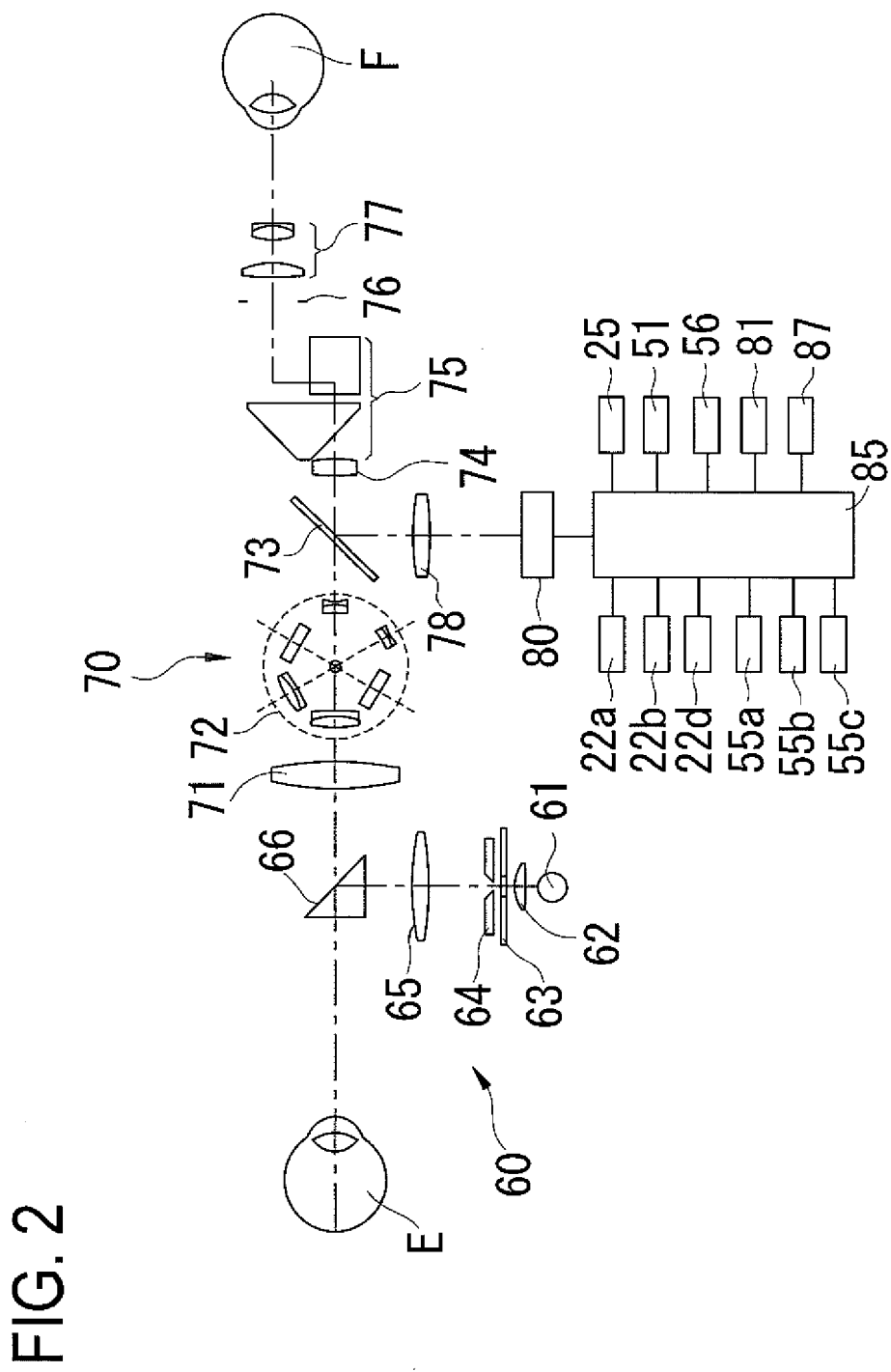
FIG. 2 is an explanatory view of optical systems of the slit lamp.
Figure 3:
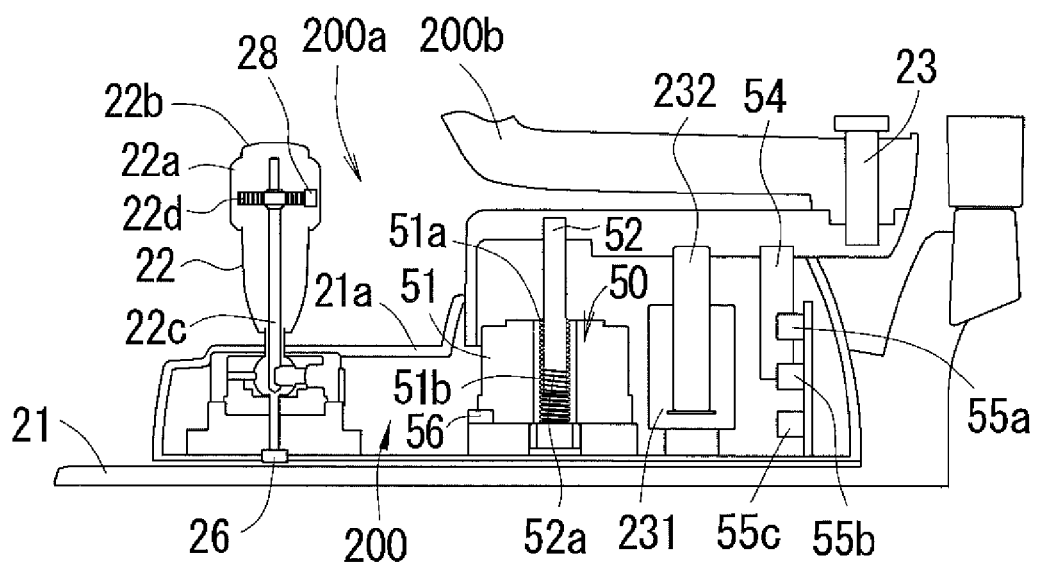
FIG. 3 is a cross sectional view of the slit lamp taken along a line A-A in FIG. 1.
Figure 4:
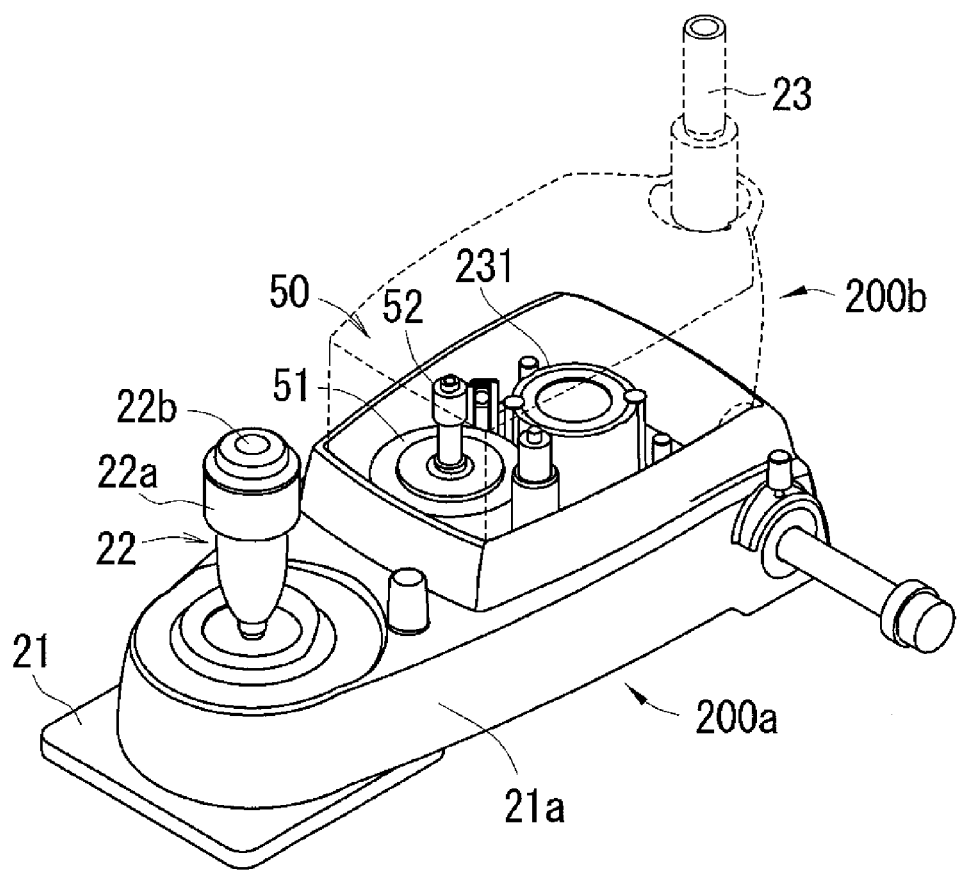
FIG. 4 is a perspective view of a main unit of the slit lamp.

A detailed description of a preferred embodiment of the present invention will now be given referring to the accompanying drawings. The present embodiment exemplifies a slit lamp (a slit-lamp microscope) 100 as an ophthalmic apparatus. FIG. 1 is a perspective external view of the slit lamp 100. FIG. 2 is an explanatory view of optical systems FIG. 3 is a cross sectional view of the slit lamp 100 taken along a line A-A in FIG. 1. FIG. 4 is a perspective view of a main unit 100b of the slit lamp 100.

The slit lamp 100 mainly includes a head support unit 100a and a main unit 100b. The head support unit 100a provided on an examinee side includes a forehead rest 11 for supporting the forehead of an examinee and a chin rest 12 for supporting the chin of the examinee and is fixed to a base 21 through two posts 13. The main unit 100b includes a movable part 200b the height (vertical position) of which is adjusted with respect to a table 1 in a vertical (up and down) direction and a fixed part 200a supporting the movable part 200b.

In a housing of the movable part 200b, there are contained an illumination unit 60, a microscope unit (an observing and photographing unit) 70, and a control part 85 for controlling operations of the entire slit lamp 100. In a housing of the fixed part 200a, a vertical movement mechanism 200 is housed to move the movable part 200b up and down with respect to an examinee's eye E.

The illumination unit 60 includes a visible light source 61, a condenser lens 62, a variable aperture 63, a variable slit 64, a projection lens 65, and a prism mirror 66 and is configured to illuminate an observing site of the eye E. Light (visible light) from the visible light source 61 passes through the condenser lens 62 and illuminates the variable aperture 63 and the variable slit 64. Then, the light passing through the variable aperture 63 and the variable slit 64 passes the projection lens 65, and is reflected by the prism mirror 66 and projected to the eye E. The visible light source 61 is selected from well-known light sources such as a halogen lamp and an LED.

The microscope unit 70 includes an objective lens 71, a variable-power optical system 72, a half mirror 73, image forming lenses 74, an erect prism 75, a field diaphragm 76, and eye pieces 77. Light reflected by the eye E passes through the objective lens 71, variable-power optical system 72, half mirror 73, and image forming lenses 74, and is reflected by the erect prism 75. The light reflected by the erect prism 75 passes through the field diaphragm 76 and the eye piece 77 and then comes in an eye F of an examiner.

Light reflected by the half mirror 73 passes through a relay lens 78 and enters a camera (an imaging element) 80. Used as the camera 80 is a well-known digital camera equipped with a CCD sensitive to visible light or the like. The control part 85 takes in a photographed (captured) image of the camera 80 in response to a command signal from a switch 22b mentioned later and displays the image on a monitor 87.

The vertical movement mechanism 200 of the fixed part 200a includes the base 21 fixed to the table 1, a housing 21a placed on the base 21 to be slidable in a horizontal direction (back and forth (Z), right and left (X) directions), a joystick 22 serving as an operating member placed in the housing 21a and partly extended outside through an opening not shown of the housing 21a, and a drive part 50 placed inside the housing 21a.

The joystick 22 includes a grip (a rotary part) 22a to be grasped and rotated by the examiner, a switch 22b for inputting a trigger signal for photographing (image capturing), a shaft (a support member) 22c placed extending through the joystick 22 in an almost vertical direction (Y direction), and a well-known encoder (a rotary encoder) 22d for detecting rotation angle of the grip 22a.

Figure 5:
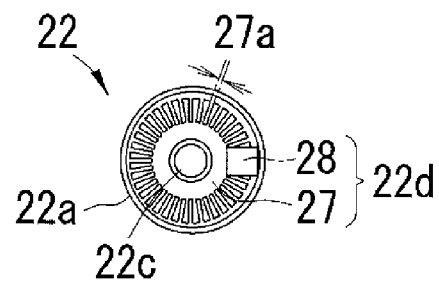
FIG. 5 is a configuration view of a rotary encoder.

FIG. 5 shows a configuration example of the encoder 22d. Herein, the encoder 22d of the joystick 22 is illustrated as being seen from the switch 22b side. The encoder 22d includes a rotating grating 27 provided rotatably in the horizontal direction together with the grip 22a, and a sensing part 28 fixed in the joystick 22 to detect the rotation angle of the rotating grating 27. For example, the sensing part 28 used in the present embodiment is a well-known photo-interrupter.

The rotating grating 27 is rotated about the shaft 22c in sync with the rotation of the grip 22a. The rotating grating 27 is formed, on its outer periphery, with a plurality of slits 27a each extending through in a thickness direction of the rotating grating 27. The slits 27a are circumferentially arranged at intervals of a predetermined rotation angle. The sensing part 28 determines a rotation amount of the grip 22a based on the number of slits 27a detected within a predetermined time. The sensing part 28 also determines a rotation speed of the grip 22a from the rotation amount of the grip 22a within the predetermined time. Even though not illustrated, the encoder 22d is provided with a well-known sensing part to detect a rotation direction of the rotating grating 27 to thereby detect a rotation direction of the grip 22a. Signals representing the rotation amount and the rotation speed detected by the sensing part 28 and a signal representing the rotation direction detected by the sensing part of the encoder 22d are outputted in the form of pulse signals to the control part 85.

Figure 6A:
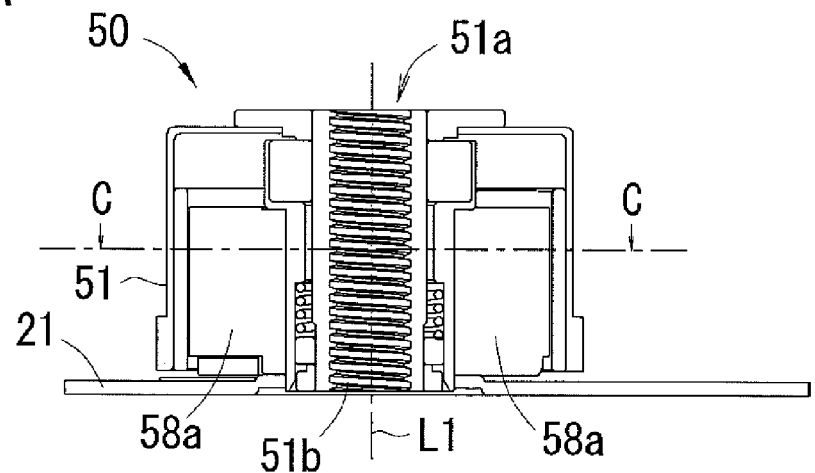
FIGS. 6A and 6B are diagrams showing a configuration of a motor.
Figure 6B:
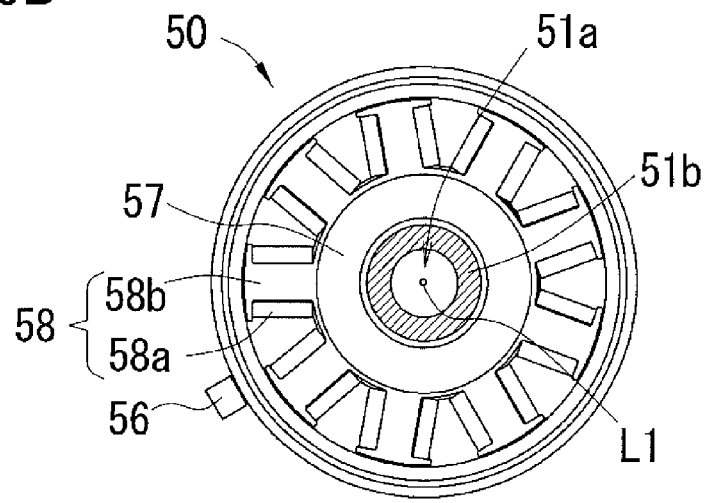

The drive part 50 includes a hollow brushless motor (hereinafter, referred to as a motor) 51 provided to be rotatable about a rotation axis L1, and a sensor 56 which is a drive sensing part to detect rotation of the motor 51. FIGS. 6A and 6B are diagrams showing a configuration of the motor 51. Specifically, FIG. 6A is a vertical sectional view of the motor 51 and FIG. 6B is a cross sectional view of the motor 51 taken along a line C-C in FIG. 6A.

The motor 51 is fixed to the housing 21a and includes a rotor 57 having a hollow portion 51a formed at the center around the rotation axis L1 and a stator 58. The rotor 57 is placed to be rotatable about the rotation axis L1 relative to the stator 58. The rotor 57 has a cylindrical shape extending in the rotation axis L1. The rotor 57 is formed, on its inner peripheral surface, with a female screw (thread) 51b. A screw hole of the female screw 51b defines the hollow portion 51a. A main part of the rotor 57 is made of a permanent magnet. The main part and the female screw 51b of the rotor 57 may be made of the same material or different material. In the case of the different material, the female screw 51b has only to be fixed to the main part of the rotor 57.

The stator 58 is fixed to the housing 21a. The stator 58 includes a well-known electromagnet. For instance, the electromagnet is formed of an iron core 58b and a winding 58a wound thereon. When an electric current is supplied to the winding 58a, a predetermined magnetic force is generated. Accordingly, when the magnetic force is generated by the electromagnet provided in the stator 58, the rotor 57 is rotated about the rotation axis L1. Furthermore, the "amount and direction" of the electric current to be applied to the winding 58a are controlled to change the rotation direction of the rotor (rotation side) 57.

The female screw (thread) 51b is formed at a predetermined pitch and engaged with a shaft 52 (a male screw 52a) of the movable part 200b mentioned later. When the female screw 51b is rotated in association with the rotation of the motor 51 (the rotor 57), the shaft 52 (the male screw 52a) is moved in the vertical (up-and-down) direction through the female screw 51b. Thus, the height of the movable part 200b in the vertical direction is changed in sync with the vertical movement of the male screw 52a.

As above, since a brushless motor is used as the motor 51 of the drive part 50, noise and vibration generated due to motor rotation are reduced as compared with a DC motor, a stepping motor, or the like in the conventional art. Since no deterioration is caused by abrasion of a brush of a motor, durability can also be increased.

The movable part 200b includes a base shaft 23 extending in a substantially vertical direction to the base 21, an arm 24 supporting the illumination unit 60, and an arm 25 supporting the microscope unit 70. The arms 24 and 25 are separately supported to be rotatable in a horizontal direction about a center axis B, so that the illumination unit 60 and the microscope unit 70 are rotated separately about the center axis B.

A shaft 52 is fixed to a lower side of the movable part 200b and is engaged with the female screw 51b of the motor 51. A distal end of the shaft 52 includes a feed screw (the male screw (thread)) 52a formed at a predetermined pitch so that the male screw 52a is engaged with the female screw 51b. When the rotation of the female screw 51b is transmitted to the male screw 52a, the movable part 200b is moved up and down at predetermined steps. The male screw 52a has only to be formed in a predetermined range of the shaft 52 so that the male screw 52a does not disengage from the female screw 51b when the movable part 200b reaches an upper limit or a lower limit of a movable range.

A lead angle of each of the female screw 51b and the male screw 52a is determined as a width that can provide a frictional force enough to keep the position of the movable part 200b so that the movable part 200b is not pressed down by its own weight when vertical movement of the movable part 200 is stopped. The lead angle is also determined in light of a minimum vertically movable range of the movable part 200b. In other words, for a small lead angle, vertically positional adjustment of the movable part 200b is conducted at smaller steps. However, such a small lead angle causes a demerit that takes a long time to move the movable part 200b up and down. The lead angle is therefore preferably determined in light of the above conditions. Furthermore, the lead angle of the female screw 51b and the male screw 52a is preferably determined in consideration of a material, a grease condition, and others.

In the present embodiment, the main part 100b is further provided with a support part separately from the shaft 52 in order to more stably move the movable part 200b up and down. For instance, this support part is constituted of a combination of a cylindrical part 231 fixed to the fixed part 200a and a rod 232 inserted in an inner hole of the cylindrical part 231 and fixed to the movable part 200b. When the movable part 200b is moved up and down, the rod 232 fixed to the movable part 200b is also moved up and down along the inner wall of the cylindrical part 231. In this manner, the movable part 200b is also held by the support part in addition to the shaft 52 and thus the vertical movement is more stable. Although the above explanation shows an example of one additional support part different from the shaft 52, a plurality of support parts may be provided.

In the embodiment, the main part 100b is further provided with a position sensing part to detect the vertical position of the movable part 200b relative to the fixed part 200a. For instance, the position sensing part consists of a plate 54 fixed to and movable together with the movable part 200b and three sensors 55a to 55c fixed to the fixed part 200a, each of the sensors 55a to 55c being formed with an opening allowing the plate 54 to pass therethrough.

When the movable part 200b is moved vertically and the plate 54 is detected by all of the three sensors 55a to 55c, the control part 85 detects that the movable part 200b is positioned at a lower limit. When the plate 54 is detected by only the sensor 55a, the movable part 200b is detected to be positioned at an upper limit. In the embodiment, furthermore, when the plate 54 is detected by the sensors 55a and 55b but is not detected by the sensor 55c, the main part 100b is considered as being located at an intermediate position (a position of an eye level marker not shown) of the movable range.

Specifically, upon operation of a switch not shown for initial alignment of the main part 100b, the motor 51 is driven to move the movable part 200b up and down until the plate 54 is detected by the sensors 55a and 55b. Thus, the movable part 200b is automatically easily adjusted to an initial position. The sensors are selectable from well-known sensors such as a photo-sensor, e.g., as a photo-interrupter, a magnetic sensor, and a mechanical sensor.

With the above configuration, the joystick 22 is slid in the horizontal direction (back and forth, right and left directions) by operation of the examiner, the main part 100b is moved by the well-known slide mechanism in the horizontal direction with respect to the examinee's eye E. On the other hand, when the grip 22a is rotated horizontally about the shaft 22c, the encoder 22d detects the rotation direction, rotation speed, and others of the grip 22a. Based on the output signal from the encoder 22d, the control part 85 controls the motor 51 (the rotor 57) to rotate based on a corresponding relationship stored in a memory 81 mentioned later between the rotation amount of the grip 22a and the rotation amount of the motor 51 (the rotor 57). When the rotor 57 is rotated under driving control of the control part 85, the male screw 52a is moved up and down along the female screw 51b formed in the hollow portion 51a, thereby moving the entire movable part 200b up and down.

The control part 85 drives and controls the entire apparatus. To the control part 85, there are connected the above grip 22a, switch 22b, encoder 22d, sensors 55a to 55c, motor 51, sensor 56, monitor 87, and further the memory 81 and others. The memory 81 stores the rotation pulse (rotation amount) of the motor 51 in association with the rotation pulse (rotation amount) of the joystick 22 (the grip 22a) detected by the encoder 22d. The memory 81 further stores the rotation direction of the joystick 22 detected by the encoder 22d and the rotation direction of the motor 51 are stored in association with each other. Based on the input signal from the joystick 22, the control part 85 directly controls the rotation amount and the rotation direction of the motor 51. The control part 85 detects the rotation state of the motor 51 based on the rotation amount and rotation speed of the motor 51 detected by the sensor 56 and controls the motor 51 to properly operate based on the input signal from the joystick 22.

Operations of the apparatus configured as above will be explained below. Prior to an examination, an examiner first turns on a power switch (not shown) of the slit lamp 100. Upon power on or by an input signal from a switch not shown, the control part 85 drives the motor 51 to move the main part 100b up and down to adjust the height of the movable part 200b to an initial state based on a detection result of the position sensing part. The examiner then asks an examinee to hold his/her head on the head support unit 100a and makes alignment of the main part 100b with the eye E of the examinee.

By horizontal movement of the joystick 22, the eye E and the main part 100b are aligned in back and forth, right and left directions. Then, the height of the main part 100b (the illumination unit 60 and the microscope unit 70) is adjusted to the eye E. To be concrete, when the examiner rotates the grip 22a of the joystick 22, its rotation amount, rotation speed, and rotation direction are detected by the well-known encoder 22d, which outputs a detection result to the control part 85.

Based on the output signal from the encoder 22d, the control part 85 directly controls the rotation amount and the rotation direction of the motor 51 without using a mechanical configuration such as a gear. When the motor 51 (the rotor 57) is rotated, the male screw 52a engaged with the female screw 51b is moved up or down, thereby changing the height (vertical position) of the movable part 200b with respect to the fixed part 200a. At that time, the detection signals representing the rotation angle and rotation direction of the motor 51 from the sensor 56 are fed back to the control part 85. Accordingly, it is detected whether or not the operation of the motor 51 is proper. In case the rotation amount of the motor 51 is insufficient, for example, the control part 85 compensates the rotating operation of the motor 51.

When the movable part 200b is to be moved in a vertically inverse direction, the examiner reversely rotates the joystick 22 (the grip 22a). Based on the signal from the encoder 22d, the control part 85 causes the motor 51 to reversely rotate. As above, the vertical movement of the movable part 200b is controlled in association with the rotation of the joystick 22. In the embodiment, the rod 232 of the support part is moved up and down in sync with the movement of the movable part 200b, so that the movement of the entire movable part 200b is further stabilized.

When the movable part 200b is moved up and down by rotating operation of the joystick 22 and the plate 54 is detected by the sensors 55a to 55c, the control part 85 determines whether or not the movable part 200b has reached a movement limit position (upper limit or lower limit). For instance, when the plate 54 is detected by all of the sensors 55a to 55c, the control part 85 determines that the movable part 200b has reached the lower movement limit position and stops driving of the motor 51 irrespective of presence or absence of the input signal from the joystick 22. Similarly, when the plate 54 is detected by only the sensor 55a, the control part 85 determines that the movable part 200b has reached the upper movement limit position and stops driving of the motor 51 irrespective of presence or absence of the input signal from the joystick 22. Then, after detecting that the movable part 200b has reached the movement limit position, the control part 85 ignores (disables) the signal from the encoder 22d even when the joystick 22 is rotated and the signal is inputted from the encoder 22d. Accordingly, it is possible to prevent the occurrence of defects due to the vertical movement of the movable part 200b beyond its movable range.

It may be arranged so that when the control part 85 detects that the movable part 200b has reached the upper or lower movement limit position, only a signal representing a specific rotation direction of the joystick 22 is ignored. In one example, when the control part 85 detects that the movable part 200b has reached to the lower limit, a signal from the joystick 22 (the encoder 22d) to further move the movable part 200b downward is ignored, whereas a signal from the joystick 22 (the encoder 22d) to move the movable part 200b upward is enabled, thereby controlling the motor 51 to rotate.

After completion of alignment between the eye E and the main unit 100b, the control part 85 turns on the visible light source 61 of the illumination unit 60 to project illumination light (a light beam) to the eye E. Thus, the eye E is made observable through the microscope unit 70. While observing the eye E, the examiner rotates the grip 22a as needed to make fine alignment of the movable part 200b (the illumination unit 60 and the microscope unit 70).

The above configuration enables the movable part 200b to be quickly moved up and down. Thus, the electrically-driven joystick (an electrically-driven vertical movement mechanism) of the present embodiment can appropriately respond to fine adjustment of the movable part 200b at small steps.

Specifically, in the vertical movement mechanism in the conventional art configured to drive the movable part 200b by screw rotation through a plurality of mechanical components such as a gear, a delay time is generated before the motor rotation is transmitted to the vertically movable screw. This causes a difficulty in smooth fine adjustment of vertical movement of the movable part 200b, that is, the vertical movement has to be repeated by operation of the joystick. In the present embodiment, on the other hand, the motor rotation is directly transmitted to the vertically movable screw and thus this screw quickly responds to an input signal from the electrically-driven joystick (the electrically-driven vertical movement mechanism) 22. Accordingly, an operation response is enhanced and the movable part 200b can be moved up and down at fine steps in sync with the rotating operation of the joystick 22.

In the electrically-driven joystick (the electrically-driven vertical movement mechanism) and the mechanical joystick (the mechanical vertical movement mechanism) in the conventional arts, it is necessary to move a plurality of mechanical parts or components through the joystick to drive the motor 51. Therefore, depending on a meshing state of gears and others, a working force needed to move the movable part up and down may become large or vary with time-dependent change of the apparatus. This may lead to difficulty with fine alignment. On the other hand, according to the invention, in which the vertically movable screw is directly driven by motor rotation without using any mechanical parts, the working force needed for the operation can be reduced and made constant. In the ophthalmic apparatus having the electrically-driven vertical movement mechanism, therefore, it is possible to adjust fine alignment with an examinee's eye.

In the above configuration, it is preferable to easily present to the examiner that the movable part 200b has reached the upper or lower limit of the movable range. Specifically, as mentioned above, in the case where the slit lamp is moved up and down by use of the joystick provided with the encoder and the motor, the vertical movement of the motor can be stopped based on a detection result of the sensors. However, in this electrically-driven type, the joystick and the motor are not mechanically connected and hence the joystick is allowed to be rotated even if the movable part is applied with a limitation to the vertical movement. Accordingly, there is a case where the examiner does not quickly notice that the vertical movement of the movable part is limited. In particular, in the case of the above slit lamp or the like, the examiner operates the joystick to vertically move the main unit while peering through the binocular microscope, and thus the limitation to the vertical movement of the movable part is hard to notice.

Therefore, a brake mechanism 26 (see FIG. 3) may be provided in the joystick 22. This brake mechanism 26 is for example a well-known electromagnetic brake. In this case, when the grip 22a is turned as in the above case and a signal generated in the encoder 22d is inputted to the control part 85, the control part 85 rotates the motor 51 based on a rotation amount and a rotation direction based on the input signal. Thus, the female screw 51b is turned, thereby moving the male screw 52a upward or downward to move the movable part 200b up or down. When the plate 54 in the movable part 200b is detected by the sensor 55a or by all the sensors 55a to 55c, the control part 85 determines that the movable part 200b has reached the upper or lower movement limit position and thus drives the brake mechanism 26 to lock the rotation of the grip 22a. This makes the examiner get a feeling that the movable part 200b has reached the upper or lower limit. The examiner can obtain an operational feeling close to a feeling obtainable by a mechanical configuration.

As another alternative, the joystick 22 may be provided with a vibration actuator so that the joystick 22 is vibrated by the control part 85 when the movable part 200b has reached the movement limit position, thereby informing the examiner of the movable part 200b being located in the limit position. As another alternative, furthermore, the limit position of the movable part 200b may be informed sensuously to the examiner by various methods that stimulate his/her sense of touch.

The fact that the movable part 200b has reached the upper or lower limit may be informed by changing the light quantity of the illumination unit 60. For instance, when the movable part 200b is detected to have reached the movement limit position as mentioned above, the control part 85 lowers the light quantity (or increases the brightness) of the visible light source 61 of the illumination unit 60 for a period in which it is perceivable to the examiner. This makes it possible for the examiner to notice that the movable part 200b comes to the limit position in the movable range while observing the examinee's eye E through the microscope of the slit lamp. As an alternative, the visible light source 61 may be blinked. Further, another alternative is to change a wavelength of light emitted from the visible light source 61 or the like, thereby informing that the movable part 200b is located in the movement limit position. The lighting state of the illumination unit 60 may also be changed between the upper limit and the lower limit in the movable range to distinctly inform of which limit position the movable part 200b is in.

In the above configured ophthalmic apparatus, the rotation amount of the motor 51 is determined according to the rotation amount of the joystick 22 (the grip 22a) detected by the encoder 22d. Accordingly, there is a case where the movable part could not be largely (quickly) moved up and down as compared with the mechanical joystick that is rotated through inertia to some extent after the examiner strongly rotates the joystick (the grip) and then leaves his/her hand from the joystick. On the other hand, in a case where a laser delivery system is mounted in a slit lamp to perform laser irradiation, for example, it is necessary to make fine alignment in a vertical direction by operation of the joystick 22.

Therefore, the rotation amount of the motor 51 (the vertical moving amount of the movable part 200b) may be controlled according to the operation speed of the joystick 22 (the rotation speed of the grip 22a). For instance, the rotation speed of the motor 51 to the rotation speed of the grip 22a is set stepwise (or linearly) and stored in the memory 81. When the rotation speed of the joystick 22 is slow and the control part 85 judges it as a small adjustment operation, a minimum pitch (a lead angle) of vertical movement by the rotation of the motor 51 is set to be fine (small) (e.g., 10 μm).

On the other hand, when the rotation of the joystick 22 is fast and the control part 85 judges it as a coarse adjustment operation, the minimum pitch of vertical movement by the rotation of the motor 51 is set to be rough (large) (e.g., 50 μm). In other words, the minimum pitch of vertical movement determined as the small adjustment operation is set to be smaller than the minimum pitch of vertical movement determined as the coarse adjustment operation. Accordingly, when the joystick 22 is rotated at a high speed, the movable part 200b can be largely moved up and down. This can achieve quick alignment. When the joystick 22 is rotated at a low speed, on the other hand, the movable part 200b can be moved up and down at fine (small) steps. This can achieve fine alignment.

As compared with the mechanical joystick whereby the movable part 200b is directly moved up and down, the electrically-driven joystick may lead to a situation that the vertical movement of the movable part 200b is rough and discrete if the encoder 22d has a low detection accuracy of the rotation angle.

Figure 7A:
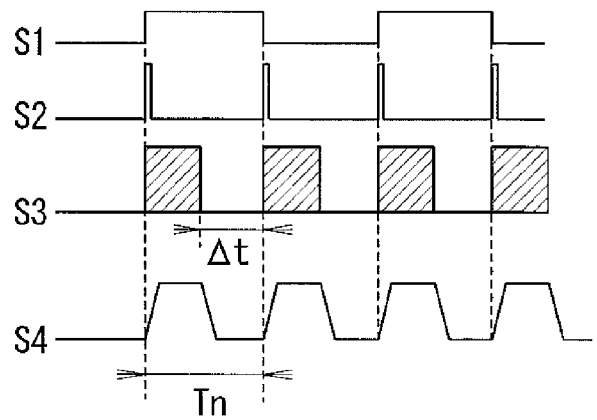
FIGS. 7A to 7C are charts to explain driving control of the motor.
Figure 7B:
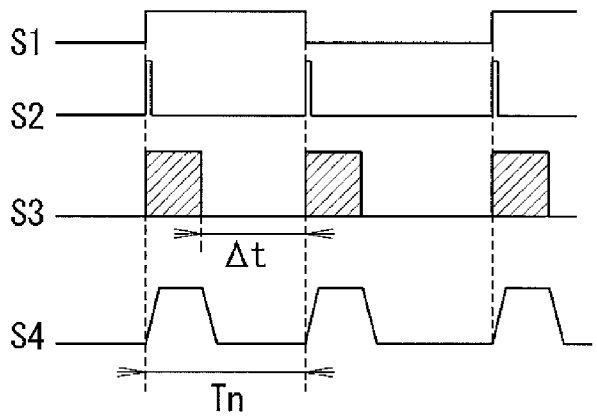
Figure 7C:
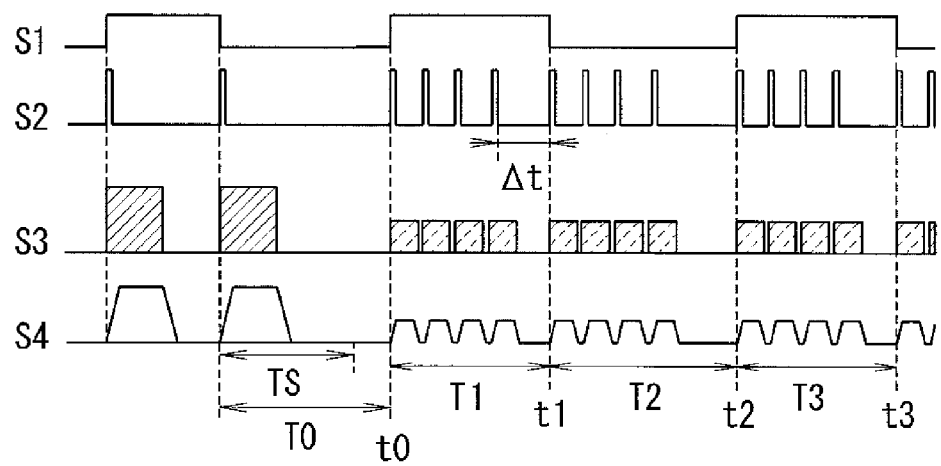

FIGS. 7A to 7C are charts to explain driving control of a motor with respect to operation signals outputted from the joystick 22 (the encoder 22d). Specifically, FIG. 7A is a chart showing driving control of the motor to the coarse adjustment operation of the joystick, FIG. 7B is a chart showing driving control of the motor to the small adjustment operation of the joystick in a conventional art, and FIG. 7C is a chart showing driving control of the motor to the small adjustment operation of the joystick in the present embodiment. In each chart, "S1" is a graph showing timing of an output signal (output pulse) of the encoder 22d, "S2" is a graph showing timing of a drive signal (drive pulse) of the motor 51, "S3" is a graph showing changes in drive amount of the motor 51, and "S4" is a graph showing changes in speed of the motor. Furthermore, the time to (n=0, 1, 2, . . . , m) is the timing at which the output pulse from the encoder 22d is inputted to the control part 85. A period (interval) Tn (n=0, 1, 2, . . . , m) is a time interval in which the output signal from the encoder 22d is continuously inputted to the control part 85. A period Δt is an off time from the end of driving of the motor 51 based on the output signal of the encoder 22d to the start of driving of the motor 51 based on a next output signal of the encoder 22d. In other words, since the motor 51 is not driven for the period Δt, the movable part 200b is not moved up and down. A threshold TS is a reference value of the time interval at which the control part 85 switches between the coarse adjustment operation and the small adjustment operation by comparison with the period Tn.

The vertical moving amount of the movable part 200b is constant with respect to the rotation amount of the grip 22a of the joystick 22. In the present embodiment, a predetermined moving amount D is set with respect to one pulse signal outputted from the encoder 22d. For instance, the rotation amount of the motor 51 to the output of the encoder 22d is determined so that the movable part 200b is moved up and down by 10 μm per one pulse from the encoder 22d and the movable part 200b is moved up and down by 4 mm per one rotation of the grip 22a.

In the conventional art, therefore, when the joystick 22 (the grip 22a) is relatively quickly rotated by the coarse adjustment operation as shown in FIG. 7A, a detection signal representing a rotation angle is continuously outputted from the encoder 22d immediately after the rotating operation of the motor 51 is completed (or during the rotating operation). In this case, the period Δt is short (or absent) and thus the motor 51 is continuously driven, thereby allowing the movable part 200b to relatively smoothly move.

On the other hand, since the height of the main unit 100b is finely adjusted by the small adjustment operation, when the grip 22a is slowly turned, the period Tn after the stop of the vertical movement of the movable part 200b by the driving control of the motor 51 to the input of the next output signal of the encoder 22d becomes long as shown in FIG. 7B. The control part 85 rotates the motor 51 based on the output signal of the encoder 22d. Accordingly, as the timing of the output signal of the encoder 22d is delayed, the period Δt is long, resulting in the discrete vertical movement of the movable part 200b by driving of the motor 51. If the movable part 200b is not smoothly moved up and down, generating vibrations, the examinee may feel a discomfort.

In the ophthalmic apparatus of the present embodiment, therefore, the threshold TS that is an interval (period) of output signals of the encoder 22d to be judged as the small adjustment operation is stored in the memory 81 as shown in FIG. 7C. When the period Tn of the output signals continuously outputted from the encoder 22d is equal to or more than the threshold TS (Tn≥TS), the control part 85 determines the operation of the joystick 22 as being switched from coarse adjustment operation to small adjustment operation and thus drives and controls the motor 51 in a division pattern (with pulse output to the motor 51 to provide a drive amount corresponding to a several multiple of the pulse output of the encoder 22d) with respect to the rotation of the encoder 22d. The drive amount represents a rotation angle of the motor per one drive signal (e.g. drive pulse). The sensor 56 that detects the rotation angle of the motor 51 is a sensor capable of detecting an angle with higher accuracy than the encoder 22d.

For instance, in FIG. 7C, it is premised that a signal (pulse) is outputted from the encoder 22d to the control part 85 at the time to (n=0, 1, 2, ..., m). The rotation speed (period) of the joystick 22 is also referred to as T1 for the time t0 to t1, T2 for the time t1 to t2, and T3 for the time t2 to t3. As illustrated, in the period Tn before the time to, the coarse adjustment operation is performed. At the time t0, on the other hand, when the control part 85 determines that the time T0 is equal to or larger than the threshold TS stored in the memory 81, the control part 85 judges that the operation of the grip 22a is switched from the coarse adjustment operation to the small adjustment operation and thus drives the motor 51 in the division pattern with respect to the rotation of the encoder 22d. For instance, the control part 85 outputs the drive pulse to drive the motor 51 in the form of pulses of a several multiple (N times (N≥2)) of one pulse output of the encoder 22d. The control part 85 multiplies the moving amount D (moving pitch) per one drive pulse during the coarse adjustment operation by an inverse number, 1/N, of the number (magnification) of drive pulses to the motor 51 and sets the moving amount (D/N) per one drive pulse during the small adjustment operation. In other words, the control part 85 multiplies the number of drive pulses by N times and controls the motor 51 at the moving amount (D/N) per one drive pulse and thereby controls the vertical movement (distance and steps) of the movable part 200b. In the case of coarse adjustment operation, specifically, the motor 51 is driven by one pulse with respect to one pulse of the encoder 22d to vertically move the movable part 200b at a predetermined distance in one step. The moving amount per one drive pulse is D mm.

In the small adjustment operation, in contrast, the driving of the motor 51 to one pulse output of the encoder 22d is divided into N operations to vertically move the movable part 200b at the predetermined distance in N-times steps. In the present embodiment, the moving amount per one drive is D/N mm. In the above configuration, even if the timing of pulse output of the encoder 22d is delayed, the movable part 200b is relatively slowly moved in the vertical direction until the encoder 22d outputs a next pulse. Accordingly, in sync with the operation of the joystick 22, the movable part 200b is smoothly moved up and down.

On the other hand, the moving amount of the movable part 200b to the rotation of the encoder 22d is constant and the accuracy is kept within the minimum pitch. Thus, the fine adjustment of the vertical movement of the movable part 200b is accurately performed. Since resolution power of the drive part is reduced and the number of driving operations (drive pulses) is increased, the interval of vertical movement in the small adjustment operation is decreased, thus reducing vibration. At the time t3 and subsequent, when it is determined that the interval Tn of the pulse output of the encoder 22d is smaller than the threshold TS, the control part 85 determines that the small adjustment operation has been switched to the coarse adjustment operation and switches the driving control of the motor 51 to that for the coarse adjustment operation. In the case where the drive amount of the motor 51 in the small adjustment operation remains at the time when switching to the coarse adjustment operation, the remaining drive amount may be ignored. This is because switching to the coarse adjustment operation is considered as indicating that a request of fine alignment using small adjustment operation is completed.

Based on the rotation speed of the joystick 22 to perform the small adjustment operation, the resolution power of driving of the motor 51 to the rotation of the encoder 22d may be changed. For instance, the rotation control of the motor 51 is set more finely as the rotation speed of the joystick 22 is slower. This control enables even the electrically-driven joystick to provide a smooth operational feeling close to the mechanical joystick.

The above explanation shows the example that a single threshold is prepared to switch between the small adjustment operation and the coarse adjustment operation. As an alternative, a plurality of thresholds may be stored in the memory 81 in advance, so that the small adjustment operation and the coarse adjustment operation are switched in stepwise fashion under the control of the control part 85. Accordingly, a suitable operational feeling can be obtained according to the purpose.

Furthermore, in the above explanation, the moving amount of the movable part 200b to the rotation of the encoder 22d is set constant, but the invention is not limited thereto. An alternative is to drive and control the motor 51 so that the moving amount of the movable part 200b in the small adjustment operation is smaller than the moving amount of the movable part 200b in the coarse adjustment operation. This configuration allows the vertical alignment at finer (smaller) steps than in the small adjustment operation.

Figure 8:
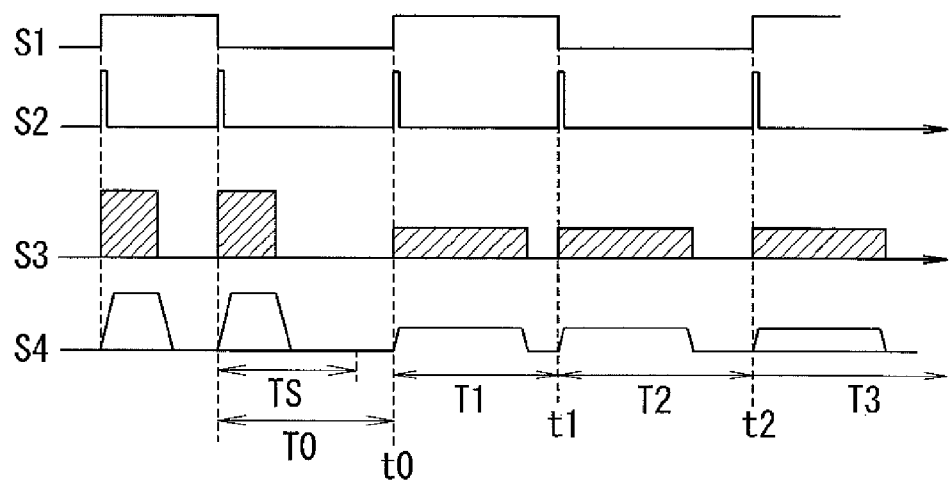
FIG. 8 is a chart to explain a modified example of the driving control of the motor.

In the above configuration, the resolution power of the drive part and the number of driving operations of the drive part per unit time are set different between in the small adjustment operation and in the coarse adjustment operation. The invention is not limited thereto and various configurations may be adopted as long as the drive time per unit time is changed. These variations can also provide a fixed effect superior to the conventional discrete motor operation. FIG. 8 shows a modified example of driving control of the motor 51 according to the invention. For instance, in the small adjustment operation, the number of driving operations of the motor 51 remains as one time and the drive time of the drive part per unit time is set longer than in the coarse adjustment operation. In this case, it is preferable to set drive voltage so as to obtain a constant drive amount to the rotation amount per unit time.

The present invention is not limited to the above may be embodied in other specific forms without departing from the essential characteristics thereof. For instance, an operation stick may be variously configured using well-known components such as a track ball to move the main unit of the ophthalmic apparatus up and down.

The above configuration is applicable to various types of ophthalmic apparatus capable of electrically moving an apparatus main unit by operation of an operation stick. These cases can also provide the same effects as above. For instance, the ophthalmic apparatus may include an eye refractive power measuring apparatus for measuring a refractive power of an eye, a fundus photographing apparatus for observing and photographing a fundus of an eye, an intraocular pressure measuring apparatus for measuring an intraocular pressure of an eye, a corneal shape measuring apparatus for measuring a corneal shape of an eye, etc.

As mentioned above, when the rotation amount of the motor 51 is changed according to the rotation speed of the joystick 22, making the operational feeling smooth, it is possible to largely (quickly) move the movable part 200b in the vertical direction as in the mechanical type and flexibly respond to fine alignment.

REFERENCE SINGS LIST

22 Joystick
50 Drive part
51 Motor
51a Hollow portion
51b Female screw
52a Male screw
60 Illumination unit
70 Microscope unit
80 Camera
100 Slit lamp
100a Head support unit
100b Main unit
200 Vertical movement mechanism
200a Fixed part
200b Movable part

The invention claimed is:

1. An ophthalmic apparatus including:
a main unit including a movable part and a fixed part, the movable part having a microscope configured to observe or photograph an examinee's eye;
the fixed part including:
a vertical movement mechanism provided with a base and a drive part configured to move the movable part up and down;
an operating member configured to be operated by an examiner to move the movable part up and down; and
a sensor configured to detect an operation signal of the operating member; and
a driving controller configured to convert the operation signal to a drive signal to move the movable part up and down, and drive the drive part based on the drive signal,
the drive part including a motor fixed to the base and being controlled by the drive controller to rotate, the motor including a stator having an electromagnet and a rotor having a hollow portion disposed about a rotation axis thereof and placed to be rotatable relative to the stator, the hollow portion being formed with a female screw, and the vertical movement mechanism including a male screw disposed in a shaft and engaged with the female screw, the male screw being fixed to and moving with the movable part, wherein the male screw is moved up and down relative to the female screw by rotation of the female screw of the rotor based on a magnetic force generated by the electromagnet to move the movable part in a vertical direction in synchronization with the vertical movement of the male screw without vertical movement of the fixed part including the motor.

2. The ophthalmic apparatus according to claim 1, wherein each of the female screw and the male screw has a lead angle determined as a width that causes no rotation due to weight of the apparatus exerted on the male screw.

3. The ophthalmic apparatus according to claim 1, further including:
a position sensor configured to detect a position of the movable part in the vertical direction;
the driving controller configured to disable the operating signal when the movable part is detected to be located in a movement limit position in the vertical direction based on a detection signal from the position sensor.

4. The ophthalmic apparatus according to claim 3, further including a drive sensor configured to detect a rotation amount of the motor,
wherein the operating member includes:
a rotation part provided configured to be rotatable in a predetermined direction when operated by an examiner to move the movable part up and down; and
a rotation sensor configured to detect a rotation amount and a rotation speed of the rotation part per unit time, and
the driving controller changes a ratio of the rotation amount of the motor based on a rotation speed of the rotation part detected by the rotation sensor and a detection result of the drive sensor.

5. The ophthalmic apparatus according to claim 4, wherein the driving controller changes a drive time of the drive part per unit time according to the rotation speed detected at every unit time based on a detection result of the rotation sensor, and increases the drive time of the drive part when the rotation speed is low compared to when the rotation speed is high.

6. The ophthalmic apparatus according to claim 5, wherein the driving controller changes a resolution power of the drive part and a number of driving operations of the drive part per unit time according to the rotation speed detected at every unit time, and increases the number of driving operations of the drive part while reducing the resolution power of the drive part when the rotation speed detected by the rotation sensor is low as compared to when the rotation speed is high.

7. The ophthalmic apparatus according to claim 5, further including:
a memory in which a threshold related to the rotation speed of the rotation part detected at every unit time is stored to determine whether operation of the rotation part operated by the examiner is a coarse adjustment operation or a small adjustment operation; and
the driving controller configured to determine the small adjustment operation when the rotation speed of the rotation part detected by the rotation sensor at every unit time is lower than the threshold and determine the coarse adjustment operation when the rotation speed of the rotation part is higher than the threshold,
wherein when the driving controller determines the small adjustment operation, the driving controller divides driving of the drive part into a predetermined division number and moves the movable part up and down by a drive amount set by multiplying the drive amount for the coarse adjustment operation by an inverse number of the predetermined division number.

* * * * *